United States Patent

Sanner et al.

Patent Number: 5,958,390
Date of Patent: Sep. 28, 1999

[54] HAIRSETTING COMPOSITIONS COMPRISING POLYSILOXANE

[75] Inventors: Axel Sanner; Wolfgang Müller, both of Frankenthal; Volker Schehlmann, Römerberg, all of Germany

[73] Assignee: BASF Aktiengesellschaft, Ludwigshafen, Germany

[21] Appl. No.: 09/034,273

[22] Filed: Mar. 4, 1998

[30] Foreign Application Priority Data

Mar. 7, 1997 [DE] Germany ............ 197 09 277

[51] Int. Cl.$^6$ .................................. A61K 7/06
[52] U.S. Cl. ........................ 424/70.1; 424/70.12
[58] Field of Search ................. 424/70.1, 70.12

[56] References Cited

U.S. PATENT DOCUMENTS 4,844,888  7/1989  Zawadzki ................. 429/69

FOREIGN PATENT DOCUMENTS

| 408 311 | 1/1991 | European Pat. Off. . |
| 412 704 | 2/1991 | European Pat. Off. . |
| 412 707 | 2/1991 | European Pat. Off. . |

*Primary Examiner*—Terressa Mosley
*Attorney, Agent, or Firm*—Keil & Weinkauf

[57] ABSTRACT

Hairsetting compositions comprise, in addition to customary auxiliaries and additives, (A) from 0.5 to 15% by weight of carboxyl-containing polymers which are water-dispersible or water-soluble in neutralized form and have a glass transition temperature of above 0° C., (B) from 0.5 to 30% by weight, based on the polymer (A) employed, of polysiloxanes containing primary, secondary or tertiary amino groups, (C) from 0 to 50% of a low molecular mass neutralizing agent.

2 Claims, No Drawings

HAIRSETTING COMPOSITIONS COMPRISING POLYSILOXANE

BACKGROUND OF THE INVENTION

Synthetic polymers have been successfully employed for setting hairstyles for almost 50 years. Initially, homopolymers and copolymers of vinyllactam were preferably employed; later on, polymers containing carboxylate groups became increasingly important. The desired set of properties, such as high strength under conditions of high atmospheric humidity, elasticity, ease of washoff from the hair, and compatibility with the other formulating components, is obtained by copolymerizing a combination of hydrophobic, elasticizing and carboxyl-containing monomers (reference: Robert Y. Lochhead, Vol. 103, December 1988, 24 ff., Rolf-Dieter Reinhardt Cosmetics and Toiletries Manufacture World Wide 1995, 189m ff.).

Although the requirements set out above are nowadays attained by various types of polymer, the handle of hairstyles set using these polymers is being perceived more and more frequently as unpleasantly dull and "not natural". Attempts to obtain an improvement by making additions to the formulations have so far led to results which are not entirely satisfactory: The addition of customary plasticizers, although improving the handle, in many cases reduces the setting effect at the same time. The polysiloxanes frequently employed are incompatible with the polar polymers and in many cases require further additives if they are to be formulated at all. Instances of separation can lead to problems both during storage of the formulation and during its use (cf. EP-A 0 408 311, p.1, line 25 et seq.).

There has therefore been no lack of attempts to bond polysiloxane groups covalently to the hairsetting polymer in order to prevent instances of separation. EP-A-0 408 311, for example, describes haircare polymers comprising a monomer which contains polysiloxane groups, together with the customary hydrophilic and hydrophobic monomers. EP-A-0 412 704 to 707 propose polymerizing polysiloxane groups, in the form of macromonomers having molar masses from 1000 to 50,000, likewise with hydrophobic and hydrophilic monomers.

The synthesis of macromonomers containing siloxane groups is extremely laborious. Because of their high molecular weight, it is virtually impossible to separate unreacted macromonomers and their unreactive impurities from the polymers. They constitute a toxicological and allergenic risk and impair the solubility. Furthermore, to obtain a good effect, the resulting copolymers can often be formulated only in combination with other polymers, carriers and further auxiliaries, as taught by the abovementioned patent documents.

BRIEF SUMMARY OF THE INVENTION

It is an object of the present invention to provide polysiloxane-containing hairsetting formulations without the disadvantages described.

DETAILED DESCRIPTION OF THE INVENTION

We have found that this object is achieved by, and thus the invention provides,
hairsetting compositions comprising, in addition to customary auxiliaries and additives,
 (A) from 0.5 to 15% by weight of carboxyl-containing polymers which are water-dispersible or water-soluble in neutralized form and have a glass transition temperature of above 0° C.,
 (B) from 0.5 to 30% by weight, based on the polymer (A) employed, of polysiloxanes containing primary, secondary or tertiary amino groups,
 (C) from 0 to 50% of a low molecular mass neutralizing agent.

Examples of suitable polymers (A), containing carboxylate groups, are copolymers of crotonic acid with vinyl esters, (meth)acrylic acid/(meth)acrylic ester with or without further nitrogen-containing comonomers, and monoesters of copolymers of maleic acid with vinyl ethers, as are customarily employed in hairsetting sprays, mousses and gels (see: Robert Y. Lochhead, Vol. 103, December 1988, 24 ff., Rolf-Dieter Reinhardt Cosmetics and Toiletries Manufacture World Wide 1995, 189m ff.).

Also suitable are carboxyl-containing polyurethanes as described in German Patent DE 42 25 045. However, it is also possible to employ polymers tailored specifically to use as hairsetting agents in accordance with the invention. In this case it is possible, for instance, to improve the ease of washoff by raising the proportion of carboxylate, or to influence setting by modifying the hydrophobic monomer content.

It is important that the polymers, in neutralized form, have a glass transition temperature of more than 0° C., preferably more than 10° C. and, in particular, more than 20° C.

The novel hairsetting compositions comprise the polymers (A) in an amount of 0.5–15, preferably 2–10% by weight.

Suitable amino-containing siloxanes (B) are, in particular, those of the following structure

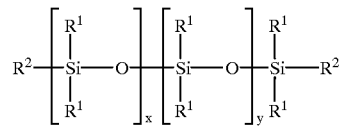

in which $R^1$ at each occurrence can be identical or different and is a group of the formula $-(CH_2)_n-R^3$ in which n can be an integer from 0 to 10.

x and y are integers such that the molecular weight of the polysiloxane block is from 300 to 30,000.

The groups $R^1$ can be selected in particular from methyl, ethyl, propyl, butyl, isobutyl, pentyl, isopentyl, hexyl, octyl, decyl, dodecyl and octadecyl, cycloaliphatic radicals, especially cyclohexyl, aromatic groups, especially phenyl and naphthyl, mixed aromatic-aliphatic radicals, such as benzyl and phenylethyl, and also tolyl and xylyl.

Each $R^2$ can be an identical or different group of the formula $-(CH_2)_n-R^3$ in which n is an integer from 0 to 10. $R^3$ can be $-H$, a member of the group of aliphatic hydrocarbons having 1 to 20 carbons, or can be aromatic. Preference extends to compounds in which at least one $R^3$ is $-N(R^4)_2$, in which $R^4$ is $-H$, or can be from the group of aliphatic hydrocarbons having 1 to 20 carbons, can be aromatic, or can be an aminoalkyl having 1–12 carbons.

$R^4$ can be identical or different at each occurrence.

Particularly suitable siloxanes are those of the structure:

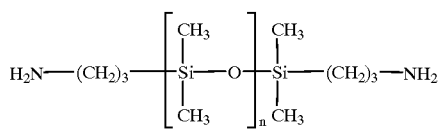

Suitable neutralizing agents (C) are, firstly, mineral bases such as sodium carbonate or potassium carbonate and ammonia, and, secondly, organic bases such as, for example, amino alcohols, especially 2-amino-2-methyl-1-propanol (AMP), triethanolamine, triisopropanolamine (TIPA), monoethanolamine, diethanolamine, tri(2-hydroxy-1-propyl)amine, 2-amino-2-methyl-1,3-propanediol (AMPD) or 2-amino-2-hydroxymethyl-1,3-propanediol, and also diamines, for example lysine.

For use in the novel hairsetting compositions the carboxyl groups of the copolymers are neutralized judiciously to the extent of from 5 to 100%, preferably from 30 to 95%.

The novel mixtures are employed, for example, as hair gels, liquid hairsetting compositions, hair mousses and, in particular, as hair sprays.

In many cases it is judicious in addition to employ further polymers in proportions of from 0.1 to 15% by weight, preferably from 1 to 5% by weight, based on the formulation.

Particularly suitable additional polymers are polymers and copolymers of N-vinyllactams and vinylamides, for example vinylpyrrolidone, vinylcaprolactam, vinylformamide and vinyl(meth)acetamide. Further suitable additional polymers are sulfo-containing polyamides, polyurethanes and polyesters, as described for example in EP 0 696 607, or DE 42 25 045 or U.S. Pat. No. 3,779,993.

EXAMPLES

| No.: | Silicone[1] | Amount[2] | Filmtransparency | Redispersibility | Smoothness[3] |
|---|---|---|---|---|---|
| 1 | — | — | + | + | − |
| 2 | Tegomer A-Si 2120 ™ | 10 | + | + | + |
| 3 | Tegomer A-Si 2320 ™ | 10 | + | + | + |
| 4 | Silikonöl IM 11 ™ | 10 | − | + | 0 |
| 5 | Tegomer A-Si 2120 ™ | 5 | + | + | + |
| 6 | Tegomer A-Si 2320 ™ | 5 | + | + | + |
| 7 | Silikonöl IM 11 ™ | 5 | − | + | 0 |
| 8 | Tegomer A-Si 2120 ™ | 2 | + | + | + |
| 9 | Tegomer A-Si 2320 ™ | 2 | + | + | + |
| 10 | Silikonöl IM 11 ™ | 2 | − | + | 0 |
| 11 | Tegomer A-Si 2120 ™ | 5 | + | + | + |
| 12 | — | — | + | + | − |
| 13 | Tegomer A-Si 2120 ™ | 5 | + | + | + |
| 14 | — | — | + | + | − |
| 15 | Tegomer A-Si 2120 ™ | 5 | + | + | + |
| 16 | — | — | + | + | − |

[1] The silicones Tegomer A-Si 2320 and Tegomer A-Si 2120 can be obtained from Goldschmidt AG; Silikonöl [silicone oil] IM 11 from Wacker. The siloxanes Tegomer A-Si 2320 and Tegomer A-Si 2120 have the following structure, where n is about 10 (A-Si 2120) or about 30 (A-Si 2320).

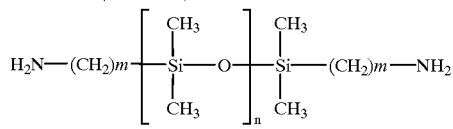

The siloxane IM 11 from Wacker has the following structure (n is about 11):

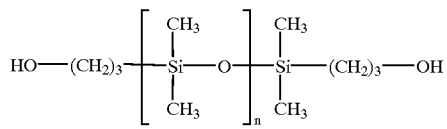

[2] % by weight based on acid-containing polymer
[3] The smoothness of the films was determined by a sensory test on films which had been knife-coated onto glass plates. This test examined both the surface roughness and the frictional characteristics.

Example 1

A 10% strength by weight solution of a t-butyl acrylate/ethyl acrylate/methacrylic acid terpolymer (Luvimer 100 p™ from BASF AG, Ludwigshafen) in ethanol is adjusted to a pH of 9.5 with 2-amino-2-methyl-1-propanol (AMP). This formulation gives transparent, water-redispersible films.

Examples 2–4

In analogy to Example 1, the following formulations were prepared with 10% by weight of the siloxanes Tegomer A-Si 2120, Tegomer A-Si 2320 and Silikon IM 11:

100 ml of ethanol 10 g of a t-butyl acrylate/ethyl acrylate/methacrylic acid terpolymer (Luvimer™ from BASF AG, Ludwigshafen)

1 g of the corresponding siloxane

AMP ad pH 9.5

Examples 5–7

In analogy to Example 1, the following formulations were prepared with 5% by weight of the siloxanes Tegomer A-Si 2120, Tegomer A-Si 2320 and Silikon IM 11:

100ml of ethanol 10 g of a t-butyl acrylate/ethyl acrylate/methacrylic acid terpolymer (Luvimer 100 p™ from BASF AG, Ludwigshafen)

0.5 g of siloxane

AMP ad pH 9.5

Examples 8–10

In analogy to Example 1, the following formulations were prepared with 2% by weight of the siloxanes Tegomer A-Si 2120, Tegomer A-Si 2320 and Silikon IM 11:

100 ml of ethanol 10 g of a t-butyl acrylate/ethyl acrylate/methacrylic acid terpolymer (Luvimer 100 p™ from BASF AG, Ludwigshafen)

0.2 g of siloxane

AMP ad pH 9.5

Example 11

Formulation comprising:

100 ml of ethanol 10 g of an octylacrylamide/acrylate/butylaminoethyl methacrylate copolymer (Amphomer™ obtainable from National Starch)

0.5 g of Tegomer A-Si 2120

AMP ad pH 7.0

Example 12

Formulation comprising:

100 ml of ethanol 10 g of an octylacrylamide/acrylate/butylaminoethyl methacrylate copolymer (Amphomer™ obtainable from National Starch)

AMP ad pH 7.0

Examples 13, 14

Formulations as in Example 11 and 12 with a vinyl acetate/vinyl propionate/crotonic acid terpolymer (Luviset™ CAP from BASF AG).

Examples 15, 16

Formulations as in Example 11 and 12 with an acrylic acid/ethyl acrylate/N-t-butylacrylamide terpolymer (Ultrahold™ 8 from BASF AG).

We claim:

1. A hairsetting composition comprising, in addition to customary auxiliaries and additives,
   (A) from 0.5 to 15% by weight of carboxyl-containing polymers which are water-dispersible or water-soluble in neutralized form and have a glass transition temperature of above 0° C.,
   (B) from 0.5 to 30% by weight, based on the polymer (A) employed, of polysiloxanes containing primary, secondary or tertiary amino groups,
   (C) from 0 to 50% of a low molecular mass neutralizing agent.

2. A hairsetting composition as claimed in claim 1, wherein the polysiloxane (B) contains more than one amino group.

* * * * *